(12) United States Patent
Latner et al.

(10) Patent No.: US 10,172,359 B2
(45) Date of Patent: Jan. 8, 2019

(54) SOLVENT SYSTEM FOR USE WITH SPOT-ON PESTICIDE COMPOSITIONS

(71) Applicant: Sergeant's Pet Care Products, Inc., Omaha, NE (US)

(72) Inventors: Matt Latner, Omaha, NE (US); James McElroy, Omaha, NE (US); Roslyn White, Omaha, NE (US); Mark Levin, Papillion, NE (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 15/598,123

(22) Filed: May 17, 2017

(65) Prior Publication Data

US 2018/0332853 A1    Nov. 22, 2018

(51) Int. Cl.
| | |
|---|---|
| *A01N 53/00* | (2006.01) |
| *A01N 25/22* | (2006.01) |
| *A01N 51/00* | (2006.01) |
| *A01N 43/40* | (2006.01) |

(52) U.S. Cl.
CPC .......... *A01N 53/00* (2013.01); *A01N 25/22* (2013.01); *A01N 43/40* (2013.01); *A01N 51/00* (2013.01)

(58) Field of Classification Search
CPC ........ A01N 53/00; A01N 25/22; A01N 43/40; A01N 51/00
See application file for complete search history.

(56) References Cited

U.S. PATENT DOCUMENTS

| | | | | |
|---|---|---|---|---|
| 7,728,011 B2 * | 6/2010 | Sirinyan | ................ | A01N 53/00 424/405 |
| 2002/0098221 A1 * | 7/2002 | Taranta | .................. | A01N 25/04 424/405 |
| 2016/0174556 A1 * | 6/2016 | Donnelly | ............. | A61K 9/0017 514/341 |

FOREIGN PATENT DOCUMENTS

| | | | |
|---|---|---|---|
| CN | 101171916 A | * | 5/2008 |
| CN | 101647436 A | * | 2/2010 |

OTHER PUBLICATIONS

CN-101647436-A machine translation, pp. 1-7 (Year: 2018).*
CN-101171916-A machine translation, pp. 1-5 (Year: 2018).*

* cited by examiner

*Primary Examiner* — Andrew S Rosenthal
(74) *Attorney, Agent, or Firm* — Polsinelli PC

(57) ABSTRACT

A solvent system, and spot-on pesticide composition comprising the solvent system and a combination of active pesticidal compounds for the treatment or prevention of insect, parasite, or tick infestations in animals, specifically mammals, including dogs and cats. The solvent system is capable of allowing high concentrations of the active pesticides, while maintaining shelf life and resistance to repeated cycles of freezing and thawing normally encountered during shipping, for example.

29 Claims, No Drawings

SOLVENT SYSTEM FOR USE WITH SPOT-ON PESTICIDE COMPOSITIONS

FIELD OF THE INVENTION

The present invention relates to a solvent system, and pesticide compositions comprising the solvent system and a combination of active pesticidal compounds, which combination is useful in the treatment or prevention of insect, parasite, or tick infestations in animals, specifically mammals, including dogs and cats. Specifically, the present invention relates to a spot-on or pour-on pesticide composition comprising a neonicotinoid and a pyrethroid, and further may include an insect growth regulator. The solvent system is capable of allowing high concentrations of the active pesticides, while maintaining shelf life and resistance to cycles of freezing and thawing normally encountered during shipping and storage. The present invention further relates to methods of preparing the solvent systems and spot-on compositions comprising the solvent systems, and to methods of killing insect and pest pupae and adults on an animal by locally administering a cutaneous application of the pesticide composition between the shoulders of the animal.

BACKGROUND OF THE INVENTION

Traditional products for the treatment or prevention of insect or parasite infestation of animals include shampoo treatments, insecticidal collars, orally ingested treatments, compositions designed to treat an animal's environment, spot-on treatments, and the like. Different treatment forms offer unique benefits and drawbacks; however, the majority offer substantial disadvantages. For instance, shampoo treatments require that the treatment be applied over the entire surface of the animal and subsequently rinsed off, which is typically unpleasant for both the animal and the owner and only provides a short-term, transient treatment. Insecticidal collars require the animal to physically wear the collar for a period of time often lasting several months, which is uncomfortable and burdensome to the animal. Additionally, treatments administered orally tend to increase the possibility of side effects and are more difficult to administer to the animal. Alternatively, treatment of the animal's surroundings and habitat is often undesirable due to the fact that the treatment may cause discoloration of furniture, carpet, bedding, etc., and may also produce unpleasant odors. Thus, it is desirable to have a spot-on treatment that can be applied to the animal in smaller portions, while maintaining treatment efficacy across the entire body surface of the animal.

Spot-on compositions have been previously developed to incorporate a multitude of pesticide agents. Common agents include arylpyrazole derivatives, insect growth regulators, pyrethroids, nodulisporic acid derivatives, neonicotinoids, formamides, avermectins, and the like. All of the compounds listed herein have different mechanisms of action, and accordingly treat and prevent infestation in different manners. Consequently, the various compounds also have a variety of different adverse effects associated with treatment. The various agents may be combined in a variety of concentrations. Generally, higher concentrations of the active components result in higher pest kill rates, and more successful treatments; however, the use of higher concentrations of the active components are more expensive to make and result in a greater likelihood that the animal will suffer adverse effects from treatment. Higher concentrations of the active components are also less stable in preparations, present difficulties in solubilizing the actives, and present reduced storage stability, as the active components can precipitate or crystallize out of solution during prolonged storage at low temperature conditions and during repeated freeze-thaw cycles commonly experienced during shipping and storage. Most, if not all, currently available pesticidal formulations containing high concentrations of active compounds rely on steric repulsion to stabilize the formulation. Steric repulsion is typically achieved through the use of polymers, such as polyvinyl alcohol or polyvinylpyrrolidone (PVP), which may be further combined with surfactants to coat the surface of colloids and prevent the actives from crystallizing. However, polymers have proven to be ineffective when combined with certain solvents needed to solubilize particular active pesticide compounds.

Therefore, it would be desirable to have a spot-on pesticide composition with improved storage stability compared to commercially available products even when the compositions comprise high concentrations of active pesticides. In addition, it is an object of the invention to provide a novel solvent system that improves stability of pesticidal compositions, solubilizes the active compounds, and inhibits crystallization of the actives when exposed to freeze/thaw conditions.

SUMMARY OF THE INVENTION

One aspect of the present disclosure provides a spot-on pesticide composition for controlling pests on animals. The composition comprises one or more active pesticidal compounds and a solvent system, the solvent system comprising urea and one or more organic solvents. The composition comprises between about 50% to about 60% (w/w) of the one or more active pesticidal compounds and between about 40% to about 50% (w/w) of the solvent system.

The solvent system may comprise between about 0.5% and about 1.5% (w/w) urea and between about 98.5% and about 99.5% (w/w) of one or more organic solvents. The one or more organic solvents may be polar aprotic solvents. The polar aprotic solvents may be selected from the group consisting of acetone, acetonitrile, ethyl acetate, dichloromethane, tetrahydrofuran (THF), dimethylacetamide (DMA), dimethylformamide (DMF), dimethyl sulfoxide (DMSO), monomethylacetamide, hexamethylphosphoric triamide (HMPT), 2-Pyrrolidone, N-methylpyrrolidone (NMP), N-octylpyrrolidone, N-ethylpyrrolidone (NEP), and combinations thereof. When the one or more organic solvents are a combination of NMP and NEP, the solvent system comprises between about 40% to about 70% (w/w) NEP and between about 30% to about 60% (w/w) NMP, preferably between about 52% and about 57% (w/w) NEP and between about 52% and about 57% (w/w) NMP.

The solvent system may comprise between about 0.7% and about 1.2% (w/w) urea, preferably between about 0.8% and about 1.0% (w/w) urea. In preferred embodiments, the solvent system comprises between about 52% and about 57% (w/w) NEP, between about 52% and about 57% (w/w) NMP, and between about 0.3% and about 0.5% (w/w) urea.

The one or more active pesticidal compounds may comprise a neonicotinoid and a pyrethroid. The one or more active pesticidal compounds comprises between about 10% to about 30% (w/w) of a neonicotinoid and between about 70% to about 90% (w/w) of a pyrethroid. The one or more active pesticidal compounds may further comprise an insect growth regulator. In preferred embodiments, the one or more active pesticidal compounds comprises between about 10% to about 30% (w/w) of a neonicotinoid, between about 70% to about 90% (w/w) of a pyrethroid, and about 0.5% to about 5% (w/w) of an insect growth regulator.

In some embodiments, the spot-on pesticide composition may comprise between about 1% and about 20% (w/w) of a neonicotinoid, between about 1% and about 70% (w/w) of a pyrethroid or between about 1% to about 15% (w/w) of a neonicotinoid and between about 10% to about 60% (w/w) of a pyrethroid. Alternatively, the composition may comprise between about 5% to about 15% (w/w) of a neonicotinoid and between about 30% to about 60% (w/w) of a pyrethroid.

The neonicotinoid may be selected from the group consisting of imidacloprid, acetamiprid, nithiazine, thiamethoxam, dinotefuran, nitenpyram, thiacloprid, and clothianadin. Preferably, the neonicotinoid is imidacloprid. When the neonicotinoid is imidacloprid, the composition comprises between about 5% to about 15% (w/w) imidacloprid, preferably between about 7.5% and about 9.5% (w/w) imidacloprid.

The pyrethroid may be selected from the group consisting of permethrin, cypermethrin, cyphenothrin, etofenprox, fenvalerate, cyfluthrin, and combinations thereof. Preferably, the pyrethroid is permethrin. When the pyrethroid is permethrin, the composition comprises between about 40% to about 50% (w/w) permethrin, preferably between about 42% and about 46% (w/w) permethrin.

The composition may further comprise an antioxidant. The antioxidant is selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, p-aminobenzoic acid (PABA), butylated hydroxyanisole (BHA), butylated hydroxytoluene (BHT), and combinations thereof. When the composition comprises an antioxidant, the antioxidant is present at a concentration of between about 0.01% and about 10% (w/w), preferably at a concentration of between about 0.01% and about 5% (w/w) of an antioxidant. The antioxidant is preferably BHT, and may preferably be present at a concentration of between about 0.05% and about 1.5% (w/w).

The composition may further comprise an insect growth regulator in addition to a pyrethroid and a neonicotinoid. When the composition comprises an insect growth regulator, the insect growth regulator is present at a concentration between about 0.01% and about 20% (w/w) of an insect growth regulator, preferably at a concentration of between about 0.1% and about 5% (w/w). The insect growth regulator may be a juvenile hormone mimic, a chitin synthesis inhibitor, and combinations thereof, and may be selected from the group consisting of S-methoprene, pyriproxyfen, novaluron, and combinations thereof. Preferably, the insect growth regulator is pyriproxyfen. Preferably, pyriproxyfen is present at a concentration of between about 0.4% and about 0.5% (w/w).

The one or more solvents of the spot-on composition may be a polar aprotic solvent. The polar aprotic solvent may be selected from the group consisting of acetone, acetonitrile, ethyl acetate, dichloromethane, tetrahydrofuran (THF), dimethylacetamide (DMA), dimethylformamide (DMF), dimethyl sulfoxide (DMSO), monomethylacetamide, hexamethylphosphoric triamide (HMPT), 2-Pyrrolidone, N-methylpyrrolidone (NMP), N-octylpyrrolidone, N-ethylpyrrolidone (NEP), and combinations thereof. Preferably, the one or more organic solvents are NMP and NEP. When the one or more organic solvents are NMP and NEP, the composition comprises between about 15% to about 30% (w/w) NEP and between about 15% to about 30% (w/w) NMP, preferably about 22% to about 26% (w/w) NEP and about 18% to about 22% NMP.

The composition may comprise between about 0.1% and about 1% (w/w) urea, preferably between about 0.3% to about 0.5% (w/w) urea. In preferred embodiments, the composition comprises between about 7.5% and about 9.5% (w/w) imidacloprid, between about 42% and about 46% (w/w) permethrin, about 0.4% to about 0.5% (w/w) pyriproxyfen, between about 0.05% and about 1.5% (w/w) BHT, and about 44% (w/w) of a solvent system, the solvent system comprising about 22% to about 26% (w/w) NEP, about 18% to about 22% (w/w) NMP, and between about 0.3% and about 0.5% (w/w) urea.

Another aspect of the present disclosure provides a spot-on pesticide composition comprising between about 1% and about 20% (w/w) of a neonicotinoid, between about 1% and about 70% (w/w) of a pyrethroid, between about 0.01% and about 20% (w/w) of an insect growth regulator, about 0.01% and about 10% (w/w) of an antioxidant, between about 10% and about 98% (w/w) of a solvent system, the solvent system comprising urea and one or more organic solvents. The one or more organic solvents may be a combination of NMP and NEP. When the one or more organic solvents is a combination of NMP and NEP, the solvent system comprises about 22% to about 26% (w/w) NEP, about 18% to about 22% (w/w) NMP, and between about 0.3% and about 0.5% urea.

The neonicotinoid may be selected from the group consisting of imidacloprid, acetamiprid, nithiazine, thiamethoxam, dinotefuran, nitenpyram, thiacloprid, and clothianadin, preferably imidacloprid. When the neonicotinoid is imidacloprid, the composition comprises between about 5% to about 15% (w/w) imidacloprid, preferably between about 7.5% and about 9.5% (w/w) imidacloprid.

The pyrethroid may be selected from the group consisting of permethrin, cypermethrin, cyphenothrin, etofenprox, fenvalerate, cyfluthrin, and combinations thereof, preferably permethrin. When the pyrethroid is permethrin, the composition comprises between about 40% to about 50% (w/w) permethrin, preferably between about 42% and about 46% (w/w) permethrin.

The antioxidant may be selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, p-aminobenzoic acid (PABA), butylated hydroxyanisole (BHA), butylated hydroxytoluene (BHT), and combinations thereof. The antioxidant may be present at a concentration ranging from about 0.01% to about 10% (w/w), preferably at a concentration ranging from about 0.01% to about 5% (w/w). The antioxidant may be BHT, preferably at a concentration of between about 0.05% and about 1.5% (w/w).

The insect growth regulator may be present at a concentration of between about 0.1% and about 5% (w/w). The insect growth regulator may be a juvenile hormone mimic, a chitin synthesis inhibitor, and combinations thereof and may be selected from the group consisting of S-methoprene, pyriproxyfen, novaluron, and combinations thereof. Preferably, the insect growth regulator is pyriproxyfen. Preferably, pyriproxyfen is present at a concentration between about 0.4% and about 0.5% (w/w).

An additional aspect of the present disclosure provides a spot-on pesticide composition comprising between about 7.5% and about 9.5% (w/w) imidacloprid, between about 42% and about 46% (w/w) permethrin, about 0.4% to about 0.5% (w/w) pyriproxyfen, between about 0.05% and about 1.5% (w/w) BHT, and about 44% (w/w) of a solvent system, the solvent system comprising about 22% to about 26% (w/w) (w/w) NEP, about 18% to about 22% (w/w) NMP, and between about 0.3% and about 0.5% (w/w) urea.

Yet another aspect of the present disclosure provides solvent system for improved storage stability of spot-on pesticide compositions, wherein the solvent system comprises between about 0.5% and about 1.5% (w/w) urea and between about 98.5% and about 99.5% (w/w) of one or more organic solvents. The one or more organic solvents may be polar aprotic solvents. When the one or more organic solvents are polar aprotic solvents, the polar aprotic solvents may be selected from the group consisting of acetone, acetonitrile, ethyl acetate, dichloromethane, tetrahydrofuran (THF), dimethylacetamide (DMA), dimethylformamide (DMF), dimethyl sulfoxide (DMSO), monomethylacetamide, hexamethylphosphoric triamide (HMPT), 2-Pyrrolidone, N-methylpyrrolidone (NMP), N-octylpyrrolidone, N-ethylpyrrolidone (NEP), and combinations thereof. Preferably, the one or more organic solvents are a combination of NMP and NEP. When the one or more organic solvents are a combination of NMP and NEP, the solvent system comprises between about 40% to about 70% (w/w) NEP and between about 30% to about 60% (w/w) NMP, preferably between about 52% and about 57% (w/w) NEP and between about 52% and about 57% (w/w) NMP.

The solvent system may comprise between about 0.7% and about 1.2% (w/w) urea, preferably between about 0.8% and about 1.0% (w/w) urea. In preferred embodiments, the solvent system comprises between about 52% and about 57% (w/w) NEP, between about 52% and about 57% (w/w) NMP, and between about 0.3% and about 0.5% (w/w) urea.

Another aspect of the present disclosure provides a solvent system for improved storage stability of spot-on pesticide compositions, the solvent system comprising between about 0.5% and about 1.5% (w/w) urea, and between about 98.5% and about 99.5% (w/w) of a solvent selected from the group consisting of NMP, NEP, and combinations thereof. The solvent system may comprise between about 52% and about 57% (w/w) NEP, between about 52% and about 57% (w/w) NMP, and between about 0.3% and about 0.5% (w/w) urea.

An additional aspect of the present disclosure provides a method of preparing a spot-on pesticide composition comprising between about 1% and about 20% (w/w) of a neonicotinoid, between about 1% and about 70% (w/w) of a pyrethroid, optionally between about 0.01% and about 20% (w/w) of an insect growth regulator, optionally between about 0.01% and about 10% (w/w) of an antioxidant, and between about 10% and about 98% (w/w) of a solvent system comprising urea and one or more organic solvents. The method comprises adding the one or more organic solvents to a vessel; adding the urea and optionally the antioxidant to the vessel while providing constant agitation; adding the neonicotinoid to the vessel while providing constant agitation; heating the pyrethroid and optionally the insect growth regulator to a temperature of about 54° C.; adding the heated pyrethroid and optionally the insect growth regulator to the vessel while providing constant agitation; and providing constant agitation to create a solution.

Yet another aspect of the present disclosure provides a method of preparing a solvent system for improved storage stability of spot-on pesticide compositions, wherein the solvent system comprises between about 0.1% and about 1% (w/w) urea, and between about 98.5% and about 99.5% (w/w) of one or more organic solvents. The method comprises adding the one or more organic solvents to a vessel; and adding the urea to the vessel while providing constant agitation.

A further aspect of the present disclosure provides a method of using a solvent system to prepare a spot-on pesticide composition with improved storage stability, wherein the spot-on composition comprises between about 1% and about 20% (w/w) of a neonicotinoid, between about 1% and about 70% (w/w) of a pyrethroid, and optionally between about 0.01% and about 20% (w/w) of an insect growth regulator and about 0.01% and about 10% (w/w) of an antioxidant. The method comprises preparing a solvent system as described above; optionally adding the antioxidant while providing constant agitation; adding the neonicotinoid to the vessel while providing constant agitation; heating the pyrethroid and optionally the insect growth regulator to a temperature of about 54° C.; adding the heated pyrethroid and optionally the insect growth regulator to the vessel while providing constant agitation; and providing constant agitation to create a solution.

Another aspect of the present disclosure provides a method of killing insect and pest pupae and adults on an animal, which method comprises administering a localized cutaneous application between the shoulders of the animal, of a spot-on composition comprising between about 1% and about 20% (w/w) of a neonicotinoid, between about 1% and about 70% (w/w) of a pyrethroid, optionally between about 0.01% and about 20% (w/w) of an insect growth regulator, optionally between about 0.01% and about 10% (w/w) of an antioxidant, and between about 10% and about 98% (w/w) of a solvent system comprising urea and one or more organic solvents. The spot-on composition may comprise between about 7.5% and about 9.5% (w/w) imidacloprid, between about 42% and about 46% (w/w) permethrin, about 0.4% to about 0.5% (w/w) pyriproxyfen, between about 0.05% and about 1.5% (w/w) BHT, and about 44% (w/w) of a solvent system, the solvent system comprising about 22% to about 26% (w/w) NEP, about 18% to about 22% (w/w) NMP, and between about 0.3% and about 0.5% (w/w) urea. The animal may be a mammal, preferably a dog or a cat.

Yet another aspect of the present disclosure provides a method of killing insect and pest pupae and adults on an animal, which method comprises administering a localized cutaneous application between the shoulders of the animal, of a spot-on composition comprising between about 7.5% and about 9.5% (w/w) imidacloprid, between about 42% and about 46% (w/w) permethrin, about 0.4% to about 0.5% (w/w) pyriproxyfen, between about 0.05% and about 1.5% (w/w) BHT, and about 44% (w/w) of a solvent system, the solvent system comprising about 22% to about 26% (w/w) NEP, about 18% to about 22% (w/w) NMP, and between about 0.3% and about 0.5% (w/w) urea.

Other aspects and iterations of the disclosure are described more thoroughly below.

DETAILED DESCRIPTION OF THE INVENTION

The compositions provided herein are spot-on pesticide compositions that utilize a solvent system and combinations of certain active compounds to treat insect, parasite, or tick infestation of animals, and also prevent future infestations by prolonged treatment efficacy. The compositions of the current disclosure are useful in the treatment of many pests, especially fleas and ticks found on domesticated animals.

Importantly, it has been surprisingly discovered that a solvent system of the present disclosure provides for improved storage stability compared to commercially available products comprising the same active compounds. Specifically, the solvent systems disclosed herein are capable of providing improved stability of compositions comprising even high concentrations of active pesticides during storage, by minimizing the crystallization of active compounds after prolonged exposure to low temperature conditions and during repeated freeze-thaw cycles commonly experienced during transport and storing. The development of a solvent system that improves storage stability and inhibits crystallization of the actives in a spot-on composition is extremely beneficial since the presence of crystals in a topical formulation could lead to a higher or lower concentration of active(s) in the solid precipitate, which may be unsafe or ineffective for topical use on an animal. Alternatively, when the precipitation of active(s) occurs, the remaining liquid solution could also contain a higher or lower concentration of active(s) than the precipitate, which could also result in a solution containing a concentration of active(s) too high for safe administration on an animal or too low to be considered effective. As a result, the formulations of the present disclosure do not rely on steric repulsion using polymers and optionally, surfactants to prevent crystallization of the active compounds; instead, the actives, when combined with the solvent systems described herein, remain soluble during transport across a variety of climate zones and survive freeze/thaw conditions without crystallizing. Advantageously, the solvent systems of the present disclosure also improve solubility of active pesticidal compounds in spot-on pesticide compositions.

The solvent system, spot-on pesticide comprising the solvent system, and methods of preparing and using the solvent system and spot-on pesticide compositions are described below.

I. Spot-on Pesticide Composition

In one aspect, the present disclosure encompasses a solvent system and spot-on pesticide compositions comprising the solvent system and a combination of active pesticidal compounds. The solvent system is capable of allowing high concentrations of the active pesticides, while maintaining shelf life and resistance to repeated cycles of freezing and thawing normally encountered during shipping, for example. It should be noted that the spot-on compositions of the present disclosure do not include crystallization inhibitors. The active compounds, the solvent system, and the spot-on compositions are further described below.

a. Active Pesticidal Compounds

Spot-on pesticide compositions comprise combinations of active pesticidal compounds to treat insect, parasite, or tick infestation of animals, and to also prevent future infestations by prolonged treatment efficacy. As such, the compositions may exterminate existing pests, and prevent those pests that survive from developing and reproducing. The compositions may also halt the growth cycle and prevent pests from laying additional eggs. The compositions of the current disclosure are useful in the treatment of many pests, especially fleas and ticks found on domesticated animals, specifically mammals. Preferably, the mammals are dogs and cats.

Preferably, the active pesticides comprise a neonicotinoid and a pyrethroid, and may optionally include other active pesticides known in the art. Alternatively, the active pesticides may consist only of a neonicotinoid and a pyrethroid as the active pesticides.

The neonicotinoid may be selected from the group consisting of imidacloprid, acetamiprid, nithiazine, thiamethoxam, dinotefuran, nitenpyram, thiacloprid, and clothianadin. Neonicotinoids achieve their efficacy by binding on insect nerve receptors, causing excitation of the nerve and muscle contraction. This particular class of pesticides is known to bind to the postsynaptic nicotinic acetylcholine receptors (nAChR) and stimulate the nerves to fire off an impulse for a sustained muscular contraction, which causes a spastic paralysis. Further nerve conduction is prevented and prolonged contraction damages muscles and nerves, causing disintegration and leading to the death of the parasite.

The amount of neonicotinoid present in the composition may be equal to from about 1% to about 40% (w/w), preferably from about 1% to about 20% (w/w). In some embodiments, the neonicotinoid comprises about 20%, 19%, 18%, 17%, 16%, 15%, 14%, 13%, 12%, 11%, 10%, 9%, 8%, 7%, 6%, 5%, 4%, 3%, 2%, or 1% (w/w) of the spot-on composition. For example, the amount of neonicotinoid present in the spot-on composition may range from between about 1% to about 20% (w/w) of the total composition, and preferably ranges from between about 1% and about 15% (w/w). Most preferably, the amount of neonicotinoid present in the spot-on composition may range from between about 5% and about 15% (w/w) of the total composition. In an exemplary embodiment, the amount of neonicotinoid present in the composition is between about 7.5% and about 9.5% (w/w) of the total composition.

In a preferred embodiment of the present disclosure, the neonicotinoid is imidacloprid. In an exemplary embodiment when the neonicotinoid is imidacloprid, the amount of imidacloprid present in the composition is about 8.8% (w/w) of the total composition.

Imidacloprid is also known as N-[1-[(6-Chloro-3-pyridyl)methyl]-4,5-dihydroimidazol-2-yl]nitramide and is sold as a pesticide commercially under the name Advantage® (Bayer). The chemical structure for imidacloprid is shown below.

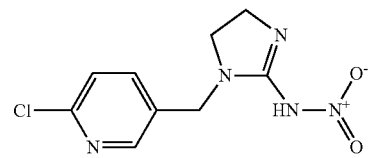 [SMILES: O=[N+]([O-])NC1=NCCN1Cc1ccc(Cl)nc1]

It is understood that analogs and associated derivatives of imidacloprid (including enantiomers, diastereomers, racemates, or pharmaceutically acceptable salts thereof) are also within the scope of the present disclosure.

The pyrethroid may be selected from the group consisting of permethrin, cypermethrin, cyphenothrin, etofenprox, fenvalerate, cyfluthrin, and combinations thereof. Generally, pyrethroids are a class of synthetic insecticides that are related to the naturally-occurring pyrethrins. Pyrethroids tend to be more effective than the natural pyrethrins, and less toxic to mammals. Pyrethroids are axonic poisons that work by keeping the sodium channels open in the neuronal membranes. The sodium channel consists of a membrane protein with a hydrophilic interior which permits sodium ions to enter and exit the membrane. When the sodium channels are kept open, the influx of sodium ions results in hyperexcitation, and the pest becomes paralyzed.

The amount of pyrethroid present in the spot-on pesticide composition is between about 1% and about 70% (w/w) of the total weight of the composition, preferably between about 10% to about 60% (w/w). In a preferred embodiment, the amount of pyrethroid present in the spot-on composition may range from about 40% to about 50% (w/w) of the total weight of the composition. For instance, in some alternatives of the embodiment, the pyrethroid comprises about 50%, 49%, 48%, 47%, 46%, 45%, 44%, 43%, 42%, 41%, or about 40% (w/w) of the spot-on composition. In an exemplary embodiment, the amount of pyrethroid present in the composition is between about 42% and about 46% (w/w) of the total composition.

In a preferred embodiment of the present disclosure, the pyrethroid is permethrin. In an exemplary embodiment when the pyrethroid is permethrin, the amount of permethrin present in the composition is between about 42% and about 46% (w/w) of the total composition.

Permethrin is sold as a pesticide commercially under trade names, some of which include Ambush, BW-21-Z, Cellutec, Ectiban, Eksmin, Exmin, FMC-33297, Indothrin, Kafil, Kestril, NRDC 143, Pounce, PP 557, Pramiex, Qamlin and Torpedo. The chemical structure for permethrin is shown below.

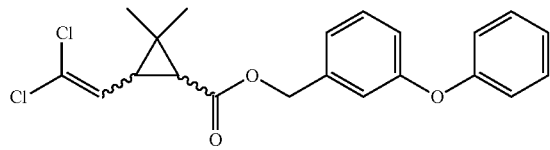 [SMILES: CC1(C)C(C=C(Cl)Cl)C1C(=O)OCc1cccc(Oc2ccccc2)c1]

It is understood that analogs and associated derivatives of permethrin (including enantiomers, diastereomers, racemates, or pharmaceutically acceptable salts thereof) are also within the scope of the present disclosure.

The spot-on pesticide composition of the present disclosure may additionally include an insect growth regulator (IGR). IGRs are not effective in killing pre-existing pests; however, they prevent reproduction and further infestation. An IGR is generally a compound that is capable of disrupting the growth and development of pest species, so that the pest cannot mature and reproduce. There are two common classes of IGRs, namely juvenile hormone mimics (or juvenoids) and chitin synthesis inhibitors (CSIs). When compositions comprise an IGR, the IGR may be a juvenoid, a CSI, or combinations thereof.

Juvenoids, such as hydroprene, methoprene, kinoprene, triprene, fenoxycarb, and pyriproxyfen, bind to juvenile hormone binding cite receptors and mimic the action of the juvenile hormones, thereby inhibiting embryogenesis, metamorphosis and adult formation. CSIs, such as novaluron, prevent the formation of chitin, a carbohydrate needed to form the insect's exoskeleton. With these inhibitors, an insect grows normally until it molts. The inhibitors prevent the new exoskeleton from forming properly, causing the insect to die. Death may be quick, or may take up to several days or months depending on the insect. CSIs can also kill eggs by disrupting normal embryonic development.

The amount of IGR present in the current disclosure may comprise between about 0.1% and about 20% (w/w) of the total weight of the spot-on composition. In some embodiments, the IGR comprises about 19%, 18%, 17%, 16%, 15%, 14%, 13%, 12%, 11%, 10%, 9%, 8%, 7%, 6%, 5%, 4%, 3%, 2%, 1%, or 0.1% (w/w) of the spot-on composition. For example, the amount of IGR present in the spot-on composition may range from between 0.1% to about 20% (w/w) of the total composition weight, and preferably the IGR ranges from between about 0.1% to about 10% (w/w) of the total composition. In an exemplary embodiment, the amount of IGR present in the composition ranges from between about 0.4% to about 0.5% (w/w).

IGRs useful in the present disclosure may include, but are not limited to, both juvenile hormone mimics and chitin synthesis inhibitors. Suitable non-limiting examples of insect growth regulators that may be used in the present disclosure include bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron, epofenonane, fenoxycarb, hydroprene, kinoprene, methoprene, pyriproxyfen, triprene, and combinations thereof. In one embodiment, the insect growth regulator is a juvenoid. Preferably, the juvenoid is pyriproxyfen.

In a preferred embodiment of the present disclosure, the IGR is pyriproxyfen. In an exemplary embodiment when the IGR is pyriproxyfen, the amount of pyriproxyfen present in the composition is about 0.4% to about 0.5% (w/w) of the total composition.

Pyriproxyfen is also known as 4-phenoxyphenyl 2-(2-pyridyloxy)propyl ether and Nylar™. The chemical structure for pyriproxyfen is shown below.

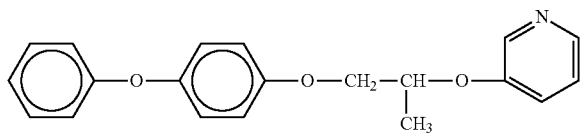

It is understood that analogs and associated derivatives of pyriproxyfen (including enantiomers, diastereomers, racemates, or pharmaceutically acceptable salts thereof) are also within the scope of the present disclosure.

In some embodiments, spot-on pesticide compositions of the present disclosure comprise between about 1% and about 20% (w/w) of a neonicotinoid, and between about 1% and about 70% (w/w) of a pyrethroid. In a preferred alternative of the embodiment, spot-on pesticide compositions comprise between about 1% to about 15% (w/w) of a neonicotinoid and between about 10% to about 60% (w/w) of a pyrethroid, preferably between about 5% to about 15% (w/w) of a neonicotinoid and between about 30% to about 60% (w/w) of a pyrethroid. In exemplary embodiments, spot-on pesticide compositions of the present disclosure comprise about 8.8% (w/w) of a neonicotinoid, and about 44% (w/w) of a pyrethroid.

In preferred embodiments, spot-on pesticide compositions of the present disclosure comprise between about 1% and about 20% (w/w) imidacloprid, and between about 1% and about 70% (w/w) permethrin. In a preferred alternative of the embodiments, spot-on pesticide compositions comprise between about 1% to about 15% (w/w) imidacloprid and between about 10% to about 60% (w/w) permethrin, preferably between about 5% to about 15% (w/w) of a imidacloprid and between about 30% to about 60% (w/w) permethrin, more preferably between about 5% to about 15% (w/w) of a imidacloprid and between about 40% to about 50% (w/w) permethrin. In exemplary alternatives of the embodiments when spot-on compositions comprise imidacloprid and permethrin, spot-on pesticide compositions comprise between about 7.5% and about 9.5% (w/w) imidacloprid and between about 42% and about 46% (w/w) permethrin.

In other preferred embodiments, spot-on pesticide compositions of the present disclosure further comprise an IGR.

In exemplary alternatives of the embodiments when spot-on compositions comprise an IGR, the IGR is pyriproxyfen, and the spot-on pesticide compositions comprise between about 0.4% and about 0.5% (w/w) pyriproxyfen.

In exemplary embodiments, spot-on pesticide compositions of the present disclosure comprise between about 7.5% and about 9.5% (w/w) imidacloprid, between about 42% and about 46% (w/w) permethrin, and about 0.4% to about 0.5% (w/w) pyriproxyfen.

It should be understood that the active components of the spot-on composition may be provided in the form of pure concentrate (100% concentration) or a diluted composition with additional excipients in the dosage form (i.e., the amount of active ingredient in the composition is less than or equal to 99.99%, and the remainder consists of inactive excipients). One of skill in the art will appreciate that the volume of active component added to the spot-on composition will need to be adjusted to account for the dilution and to ensure the end spot-on composition comprises the appropriate final concentration of each of the active components. One of skill in the art will also appreciate that the various components of the spot-on composition may be provided in a variety of dosage forms including, but not limited to, powder, briquettes, liquid solution or suspension, pellets, emulsion, aerosol, cream, gel, ointment, and the like.

b. Solvent System

As described above, spot-on compositions of the present disclosure comprise a solvent system capable of providing improved storage stability by minimizing crystallization after prolonged storage at low temperature conditions, and during repeated freeze-thaw cycles commonly experienced during shipping and storage. For instance, a solvent system of the present disclosure may provide storage stability of a spot-on composition for a duration of 1, 2, 3, 4, 5, 6, 7, 8, 9, 10, 15, 20, 30, 40, 50, or 60 or more days, even when the spot-on composition is subjected to one or more freeze/thaw cycles. Preferably, a solvent system of the present disclosure provides storage stability of a spot-on composition for a duration of 1, 2, 3, 4, 5, 6, 7, 8, 9, 10, 15, 20, 30, 40, 50, or 60 or more days, even when the spot-on composition is subjected to three or more freeze/thaw cycles.

Alternatively, a solvent system of the present disclosure may minimize crystallization of an active in a spot-on composition during 1, 2, 3, 4, 5, 6, 7, 8, 9, 10, 15, 20, 30, 40, 50, or 60 or more freeze/thaw cycles. Preferably, a solvent system of the present disclosure minimizes crystallization of an active in a spot-on composition during at least 3 freeze/thaw cycles.

A solvent system of the present disclosure generally comprises urea and one or more organic solvents. The amount of urea in a solvent system of the current disclosure may range between about 0.1 and about 5% (w/w) urea, preferably between about 0.7% to about 1.2% (w/w). In an exemplary embodiment, the amount of urea in a solvent system is between about 0.8% and about 1.0% (w/w).

The amount of the one or more organic solvents in a solvent system of the current disclosure may range between about 98.5% and about 99.5% (w/w). In an exemplary embodiment, the amount of the one or more organic solvents in a solvent system is about 99% (w/w).

The one or more organic solvents are preferably polar aprotic solvents. Suitable examples of polar aprotic solvents which may be used in the solvent system include, but are not limited to, acetone, acetonitrile (also known as cyanomethane, ethyl nitrile, methanecarbonitrile, or methyl cyanide), ethyl acetate, dichloromethane (also known as DCM or methylene chloride), tetrahydrofuran (THF), dimethylacetamide (DMA), dimethylformamide (DMF), dimethyl sulfoxide (DMSO), monomethylacetamide, hexamethylphosphoric triamide (HMPT), 2-Pyrrolidone (also known as 2-Pyrrolidinone), N-methylpyrrolidone (also known as NMP, N-methyl-2-pyrrolidone, 1-methyl-2-pyrrolidinone, or 1-methyl-2-pyrrolidone), N-octylpyrrolidone, and N-ethylpyrrolidone (also known as NEP, ethyl pyrrolidone, 1-ethyl-2-pyrrolidone, and ethyl pyrrolidinone), or combinations thereof. Exemplary solvents are selected from the group consisting of NMP, NEP, and mixtures thereof.

In one embodiment, a solvent system comprises only one polar aprotic solvent. In a preferred embodiment, a solvent system comprises a combination of two polar aprotic solvents. In an exemplary embodiment, a solvent system comprises a combination of NMP and NEP in a spot-on composition of the present disclosure. When a solvent system comprises a combination of NMP and NEP, the solvent system comprises between about 40% to about 70% (w/w) NEP and between about 30% to about 60% (w/w) NMP. In an exemplary embodiment, the solvent system comprises between about 52% and about 57% (w/w) NEP and between about 52% and about 57% (w/w) NMP.

In some embodiments, solvent systems of the present disclosure comprise between 0.1 and about 5% (w/w) urea, and between about 98.5% and about 99.5% (w/w) of the one or more organic solvents. In exemplary embodiments, a solvent system comprises between about 0.8% and about 1.0% (w/w) urea and about 99% (w/w) of the one or more organic solvents.

c. Antioxidants and Inactive Excipients

The spot-on composition may further comprise an antioxidant. An antioxidant is generally defined as a compound capable of slowing or preventing the oxidation of other molecules. Oxidation is a chemical reaction that transfers electrons from the original substance to an oxidizing agent. Oxidation reactions can produce free radicals, which start chain reactions that damage cells. Antioxidants terminate these chain reactions by removing free radical intermediates, and inhibit other oxidation reactions by being oxidized themselves. Within the spot-on composition, the antioxidant acts as a stabilizer, preventing the various components from degrading by oxidation processes. In addition, many of the commercially-available compositions that incorporate a pyrethroid including cyphenothrin have reported that the animals suffer from adverse effects including paraesthesia (a skin sensation that generally comprises feelings of prickling, itching, and tingling). However, it has been shown that inclusion of an antioxidant into the spot-on composition may help prevent the undesirable adverse effects associated with treatment regimens that include such active pesticides.

Antioxidants incorporated into the current disclosure should generally be miscible with the organic solvents described herein. The antioxidant also should not cause irritation to the skin of an animal, specifically a dog or cat, when applied to the animal's skin. In addition, the antioxidant may be natural or synthetic. Suitable antioxidants include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), *eucalyptus* extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanillic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof. One skilled in the art will appreciate that the antioxidants incorporated into the composition (including those listed herein) encompass all potential salt and ester forms of the antioxidants in addition to the pure forms of the compound. Preferably, the antioxidant comprises butylated hydroxytoluene (BHT).

In addition, the antioxidant typically comprises less than about 10% (w/w) of the total spot-on composition. In some embodiments, the antioxidant comprises about 10%, 9%, 8%, 7%, 6%, 5%, 4%, 3%, 2%, 1%, 0.1%, or about 0.01% (w/w) of the total composition. For example, the amount of antioxidant present in the spot-on composition may range from between 0.01% to about 10% (w/w) of the total spot-on composition, and preferably the antioxidant ranges from between about 0.01% to about 5% (w/w) of the total spot-on composition. In an exemplary embodiment, the antioxidant is BHT, and the amount of BHT present in a spot-on composition of the present disclosure is between about 0.05% and about 1.5% (w/w).

The spot-on composition may further include inactive excipients that are added to the composition as a result of their incorporation into the individual active components. For instance, the neonicotinoid component of the composition may be provided in a 95% solution, meaning that 95% of the neonicotinoid component volume is active pesticide and the remaining 5% constitutes inactive excipients that are consequently introduced into the composition, as such the pesticide may not be 100% pure concentrate and may be purchased with other constituents. One skilled in the art will recognize that the inactive excipients include, but are not limited to, preservatives, diluents, lubricants, pH modifiers, stabilizers, and the like. It should, however, be understood that the inactive excipients are typically incorporated as a portion of the active ingredient components and comprise a small percentage (generally less than 1%) of the total spot-on composition volume, generally not affecting the physical characteristics of the spot-on composition.

d. Spot-on Compositions

In some embodiments, spot-on pesticide compositions of the present disclosure comprise between about 1% and about 20% (w/w) of a neonicotinoid, between about 1% and about 70% (w/w) of a pyrethroid, and between about 10% and about 98% (w/w) of a solvent system, the solvent system comprising urea and one or more organic solvents. In a preferred alternative of the embodiment, spot-on pesticide compositions comprise between about 1% to about 15% (w/w) of a neonicotinoid, between about 10% to about 60% (w/w) of a pyrethroid, and between about 25% and about 89% (w/w) of a solvent system. In a preferred alternative of the embodiment, spot-on pesticide compositions comprise between about 5% to about 15% (w/w) of a neonicotinoid, between about 30% to about 60% (w/w) of a pyrethroid, and between about 25% and about 65% (w/w) of a solvent system. In exemplary embodiments, spot-on pesticide compositions of the present disclosure comprise about 8.8% (w/w) of a neonicotinoid, about 44% (w/w) of a pyrethroid, and about 47.2% (w/w) of a solvent system.

In preferred embodiments, spot-on pesticide compositions of the present disclosure comprise between about 1% and about 20% (w/w) imidacloprid, between about 1% and about 70% (w/w) permethrin, and between about 10% and about 98% (w/w) of a solvent system. In a preferred alternative of the embodiment, spot-on pesticide compositions comprise between about 1% to about 15% (w/w) imidacloprid, between about 10% to about 60% (w/w) permethrin, and between about 25% and about 89% (w/w) of a solvent system. In a preferred alternative of the embodiment, spot-on pesticide compositions comprise between about 5% to about 15% (w/w) imidacloprid, between about 30% to about 60% (w/w) permethrin, and between about 25% and about 65% (w/w) of a solvent system. In exemplary embodiments, spot-on pesticide compositions of the present disclosure comprise between about 7.5% and about 9.5% (w/w) imidacloprid, between about 42% and about 46% (w/w) permethrin, and about 47.2% (w/w) of a solvent system.

In other preferred embodiments, spot-on pesticide compositions of the present disclosure further comprise an IGR. In exemplary alternatives of the embodiments when spot-on compositions comprise an IGR, the IGR is pyriproxyfen, and the spot-on pesticide compositions comprise between about 0.4% and about 0.5% (w/w) pyriproxyfen.

In exemplary embodiments, spot-on pesticide compositions of the present disclosure comprise between about 7.5% and about 9.5% (w/w) imidacloprid, between about 42% and about 46% (w/w) permethrin, about 0.4% to about 0.5% (w/w) pyriproxyfen, between about 0.05% and about 1.5% (w/w) BHT, and about 44% (w/w) of a solvent system wherein the solvent system comprises about 22% to about 26% (w/w) NEP, about 18% to about 22% (w/w) NMP, and between about 0.3% and about 0.5% (w/w) urea.

II. Method of Preparing

In another aspect, the present disclosure encompasses a method of preparing a spot-on pesticide composition. The spot-on composition may be as described in Section I, and may comprise between about 1% and about 20% (w/w) of a neonicotinoid, between about 1% and about 70% (w/w) of a pyrethroid, optionally between about 0.01% and about 20% (w/w) of an insect growth regulator, optionally between about 0.01% and about 10% (w/w) of an antioxidant, and between about 10% and about 98% (w/w) of a solvent system comprising urea and one or more organic solvents. It should be understood that the current disclosure encompasses a variety of physical formulations; however, the spot-on compositions of the current disclosure are generally directed to liquid solutions and suspensions. The formulations of the present disclosure may be prepared by standard techniques known in the art.

In some embodiments, the spot-on pesticide compositions of the current disclosure can be produced by contacting the various active components of the spot-on composition with the various components of the solvent system to produce a spot-on formulation suitable for application to an animal's skin. In a preferred alternative of the embodiments, a method of preparing spot-on compositions of the present disclosure comprises: (a) adding the one or more organic solvents of a solvent system described in Section I(b) above to a vessel; (b) adding the neonicotinoid to the vessel while providing constant agitation; (c) optionally heating the pyrethroid and optionally heating the insect growth regulator; (d) adding the heated pyrethroid and optionally the insect growth regulator to the vessel while providing constant agitation; (e) adding the urea of a solvent system described in Section I(b) above and optionally the antioxidant to the vessel while providing constant agitation; and (f) providing constant agitation to create a solution.

Preferably, the spot-on pesticide composition of the current disclosure is produced by preparing a solvent system, and contacting the various active components of the spot-on composition with the solvent system to produce a spot-on formulation suitable for application to an animal's skin. Generally, a method of preparing a solvent system of the present disclosure comprises adding the one or more organic solvents to a vessel, and adding the urea to the vessel while providing constant agitation. Active pesticides of the spot-on composition may then be added to the solvent system to prepare a spot-on composition. In a preferred embodiment, the spot-on composition is prepared by: (a) adding the one or more organic solvents of a solvent system described in Section I(b) above to a vessel; (b) adding the urea of a solvent system described in Section I(b) above and optionally the antioxidant to the vessel while providing constant agitation; (c) adding the neonicotinoid to the vessel while providing constant agitation; (d) optionally heating the pyrethroid and optionally heating the insect growth regulator; (e) adding the heated pyrethroid and optionally the insect growth regulator to the vessel while providing constant agitation; and (f) providing constant agitation to create a solution.

In all the embodiments disclosed above, the pyrethroid and the insect growth regulator, if used, are heated to a temperature ranging from about 30° C. to about 100° C., preferably to a temperature ranging from about 40° C. to about 70° C., more preferably to a temperature ranging from about 50° C. to about 60° C. In preferred embodiments, the pyrethroid and the insect growth regulator, if used, are heated to a temperature of about 54° C.

The physical characteristics of the spot-on composition may vary depending upon the physical characteristics desired. However, the spot-on composition should be capable of application to the skin of an animal and provide adequate stasis to allow the active components of the spot-on composition to be absorbed by the host animal. Preferably, the spot-on compositions of the present disclosure have low viscosity. Viscosity is the measurement of flow resistance due to internal friction within the fluid, and is measured in centistokes (cSt). A lower cSt measurement means the fluid will flow with less resistance because of minimal molecular friction within the fluid. The lower the viscosity, the faster the fluid will flow. High viscosity substances are liquids that are thick and gelatinous in nature with slow flow. Low viscosity substances exhibit a fast flow, with an example being water at room temperature (water at 20° C. has a viscosity of about 1 cSt; 1 cSt=1 mm$^2$/second). The spot-on compositions of the present disclosure typically have a viscosity ranging from about 0.01 mm$^2$/second to about 100 mm$^2$/second. In a more preferred embodiment, the spot-on composition has a viscosity ranging from about 1 mm$^2$/second to about 30 mm$^2$/second. In a further preferred embodiment, the spot-on composition has a viscosity ranging from about 4 mm$^2$/second to about 20 mm$^2$/second.

III. Method of Killing Pests

In an additional aspect, the present disclosure encompasses a method of killing pest pupae and adults on an animal comprising administering a localized cutaneous application of a spot-on composition between the shoulders of the animal. The spot-on composition may be as described in Section I and may comprise between about 1% and about 20% (w/w) of a neonicotinoid, between about 1% and about 70% (w/w) of a pyrethroid, optionally between about 0.01% and about 20% (w/w) of an insect growth regulator, optionally between about 0.01% and about 10% (w/w) of an antioxidant, and between about 10% and about 98% (w/w) of a solvent system comprising urea and one or more organic solvents.

The compositions and methods according to this disclosure are intended for application to animals, in particular dogs and cats, and are generally applied by deposition onto the skin ("spot-on" or "pour-on" application). Treatment typically comprises a localized application over a surface area of less than 10 cm$^2$, especially of between 5 and 10 cm$^2$. Generally, the spot-on composition should be applied to an area where the animal cannot lick the application area, as licking of the application area may lead to transient adverse effects, such as excessive salivation. In particular, application is preferred at two points and preferably localized between the animal's shoulders. After the spot-on composition has been applied, the composition diffuses, in particular over the animal's entire body, and then dries without crystallizing or modifying the appearance (in particular absence of any whitish deposit or dusty appearance) or the feel of the animal's fur. Further, the method of the current disclosure is directed to application of the spot-on composition to the skin of the animal every four weeks to ensure continuous treatment and prevention of pest infestation. Typically, the active constituents are applied to the host animal together in a single formulation.

In a preferred embodiment of the disclosure, the method of killing insect and pest pupae and adults on an animal, comprises administering a localized cutaneous application between the shoulders of an animal, a spot-on composition comprising about 8.8% (w/w) imidacloprid, between about 42% and about 46% (w/w) permethrin, between about 7.5% and about 9.5% (w/w) imidacloprid, about 0.4% to about 0.5% (w/w) pyriproxyfen, between about 0.05% and about 1.5% (w/w) BHT, and about 44% (w/w) of a solvent system, the solvent system comprising about 22% to about 26% (w/w) NEP, about 18% to about 22% (w/w) NMP, and between about 0.3% and about 0.5% (w/w) urea. This method can be used to treat any animal, but it is very desirable for treating dogs.

In an alternative embodiment, the method of killing insects is carried out such that the spot-on composition is applied in a volume sufficient to deliver a dosage of the active neonicotinoid component in an amount ranging from between about 0.1 mg/kg to about 40 mg/kg of host animal body weight. In a preferred embodiment, the dose of neonicotinoid ranges from about 2 mg/kg to about 20 mg/kg of host animal body weight. In a more preferred embodiment, the spot-on composition application comprises a volume sufficient to deliver a neonicotinoid dose ranging from about 5 mg/kg to about 15 mg/kg of host animal weight.

In another embodiment, the method of killing insects is carried out such that the spot-on composition is applied in a volume sufficient to deliver a dosage of the active pyrethroid component ranging from about 0.1 mg/kg to about 40 mg/kg of host animal body weight. In a preferred embodiment, the dose of pyrethroid ranges from about 0.5 mg/kg to about 20 mg/kg of host animal body weight. In a more preferred embodiment, the spot-on composition application comprises a volume sufficient to deliver a pyrethroid dose ranging from about 0.5 mg/kg to about 10 mg/kg of host animal body weight.

In a further embodiment, the method of killing insects is carried out such that the spot-on composition further comprises an IGR, and is applied in a volume sufficient to deliver a dosage of the insect growth regulating active component ranging from about 0.1 mg/kg to about 40 mg/kg of host animal body weight. In a preferred embodiment, the dose of insect growth regulator ranges from about 0.2 mg/kg to about 20 mg/kg of host animal body weight. In a more preferred embodiment, the spot-on composition application comprises a volume sufficient to deliver an insect growth regulator dose ranging from about 0.5 mg/kg to about 10 mg/kg of host animal body weight.

One of skill in the art will understand that the dosage ranges provided above are approximate values that may vary within a broad range. The variance in dose is due to the fact that, in practice, the spot-on composition will be administered in defined doses and volumes to animals within a certain range of weights. As a result, the dosage actually applied to the animal may vary by a factor ranging from 0.1 to 10 relative to the preferred dose, without imparting any additional risks pertaining to toxicity or decreased efficacy.

Although the components of the composition are effective against a wide variety of pests and parasites, the composition is especially developed for the treatment of fleas (including the *Ctenocephalides* species) and ticks (the *Rhipecephalus*, *Ixodes*, and *Trichodectes* species). Furthermore, the frequency of application may be varied according to the needs of the individual animal, as well as the severity of infestation. The treatment of fleas may be repeated as often as once weekly, or may be reserved for one-time acute treatments of flea infestation or flare-ups. In one embodiment of the current disclosure, the treatment of fleas may be repeated about every four weeks, five weeks, or six weeks. In another embodiment, the spot-on composition is applied to the host animal for a one-time treatment of the pest infestation. With regard to the treatment of ticks, the application schedule for the spot-on composition will vary depending on the type of tick being treated. It is generally recommended that treatment of paralytic ticks (*Ixodes* species) occur more frequently than other species. In an embodiment of the current disclosure, paralytic ticks are treated at a frequency ranging from one to four weeks, with treatment every two weeks being preferred. Other genera of ticks generally have a treatment schedule similar to treatment of flea infestation, preferably ranging from approximately four to six weeks. In another embodiment, the spot-on composition is applied on a one-time basis for the treatment of tick infestation.

Although the disclosure described herein is susceptible to various modifications and alternative iterations, specific embodiments thereof have been described in greater detail above. It should be understood, however, that the detailed description of the spot-on composition is not intended to limit the disclosure to the specific embodiments disclosed. Rather, it should be understood that the disclosure is intended to cover all modifications, equivalents, and alternatives falling within the spirit and scope of the disclosure as defined by the claim language.

Definitions

Unless otherwise defined, all technical and scientific terms used herein have the same meaning as is commonly understood by one of skill in the art to which this disclosure belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight" and is used to describe the concentration of a particular substance in a mixture or solution. As used herein, "w/w" describes the concentration of a particular substance either in the spot-on pesticide formulation or in the solvent system, as noted.

As used herein, the term "mL/kg" designates milliliters of composition per kilogram of body weight.

As used herein, the term "a.i." designates active ingredient.

As used herein, the term "treatment" or "treating" of a condition, such as pest infestation, includes inhibiting an existing condition or arresting its development; or ameliorating or causing regression of the condition. The term "preventing" or "prevention" of a condition, such as insect or pest infestation, includes substantially blocking or inhibiting the development or growth of a condition before it starts. Compositions that treat or prevent infestations herein will preferably exhibit at least 90% efficacy.

As used herein, the term "pesticide" or "pesticidal" refers to an agent or a composition comprising an agent that is capable of preventing, reducing or eliminating pest infestations. Pesticides of the present disclosure generally include a neonicotinoid and a pyrethroid. Preferably, the pesticides of the present disclosure comprise imidacloprid and permethrin.

As used herein, the term "insect growth regulator" or "IGR" refers to an agent that is capable of interrupting or inhibiting the life cycle of a pest such that the pest never matures into an adult and becomes incapable of reproducing. A preferred IGR of the present disclosure includes pyriproxyfen.

As used herein, the term "animal" refers to a mammal, specifically a companion animal, including but not limited to dogs, cats, rabbits, ferrets, horses, and hamsters.

As used herein, the term "pest" and "insect" refers to any ectoparasite, including but not limited to fleas, ticks, flies, keds, mosquitoes, and mites.

EXAMPLES

The following examples are intended to further illustrate and explain the present disclosure. The disclosure, therefore, should not be limited to any of the details in these examples.

Example 1—an Imidacloprid/Permethrin/Pyriproxyfen Spot-on Pesticide Composition Comprising 0.1% Urea A spot-on pesticide composition can be made in accordance with the formulation provided in Table 1:

TABLE 1

Spot-on Pesticide Composition Comprising Imidacloprid, Permethrin, Pyriproxifen, and 0.1% Urea

| Purity | Ingredient | Amount for 500 gm | Purity Adjusted Concentration (%) |
|---|---|---|---|
| 96.4 | Imidacloprid (98.3%) | 45.58 | 9.12 |
| 95.3 | Permethrin (95.2%) | 230.35 | 46.07 |
| 98.7 | Pyriproxyfen (98.7%) | 2.23 | 0.45 |
| N/A | Urea | 0.50 | 0.10 |
| N/A | N-methylpyrrolidone | 100.00 | 20.00 |
| N/A | N-Ethylpyrrolidone | 120.84 | 24.17 |
| N/A | BHT | 0.5 | 0.10 |
|  | TOTAL | 500.0 | 100.00 |

The N-methylpyrrolidone and N-Ethylpyrrolidone were added to a >500 ml beaker. Imidacloprid was added to the beaker while mixing. With continued mixing, permethrin (pre-heated to 54° C.) was added to the main mixture, followed by the addition of pyriproxyfen (pre-heated to 54° C.). BHT and urea were added separately to the beaker with constant mixing after each addition until a clear homogenous solution was formed (about 1 hour).

The composition was stored/frozen at a temperature of −23.3° C. for about 24 hours and then thawed. Slight crystal growth was observed after the freeze/thaw cycle.

Example 2—an Imidacloprid/Permethrin/Pyriproxyfen Spot-on Pesticide Composition Comprising 0.2% Urea A spot-on pesticide composition can be made in accordance with the formulation provided in Table 2:

TABLE 2

Spot-on Pesticide Composition Comprising Imidacloprid, Permethrin, Pyriproxifen, and 0.2% Urea

| Purity | Ingredient | Amount for 500 gm | Purity Adjusted Concentration (%) |
|---|---|---|---|
| 96.4 | Imidacloprid (98.3%) | 45.58 | 9.12 |
| 95.3 | Permethrin (95.2%) | 230.35 | 46.07 |
| 98.7 | Pyriproxyfen (98.7%) | 2.23 | 0.45 |
| N/A | Urea | 1.00 | 0.20 |
| N/A | N-methylpyrrolidone | 100.00 | 20.00 |
| N/A | N-Ethylpyrrolidone | 120.34 | 24.07 |
| N/A | BHT | 0.5 | 0.10 |
|  | TOTAL | 500.0 | 100.00 |

The N-methylpyrrolidone and N-Ethylpyrrolidone were added to a >500 ml beaker. Imidacloprid was added to the beaker while mixing. With continued mixing, permethrin (pre-heated to 54° C.) was added to the main mixture, followed by the addition of pyriproxyfen (pre-heated to 54° C.). BHT and urea were added separately to the beaker with constant mixing after each addition until a clear homogenous solution was formed (about 1 hour).

The composition was stored/frozen at a temperature of −23.3° C. for about 24 hours and then thawed. Minimal crystal growth was observed after the freeze/thaw cycle.

Example 3—an Imidacloprid/Permethrin/Pyriproxyfen Spot-on Pesticide Composition Comprising 0.3% Urea A spot-on pesticide composition can be made in accordance with the formulation provided in Table 3:

TABLE 3

Spot-on Pesticide Composition Comprising Imidacloprid, Permethrin, Pyriproxifen, and 0.3% Urea

| Purity | Ingredient | Amount for 500 gm | Purity Adjusted Concentration (%) |
|---|---|---|---|
| 96.4 | Imidacloprid (98.3%) | 45.58 | 9.12 |
| 95.3 | Permethrin (95.2%) | 230.35 | 46.07 |
| 98.7 | Pyriproxyfen (98.7%) | 2.23 | 0.45 |
| N/A | Urea | 1.50 | 0.30 |
| N/A | N-methylpyrrolidone | 100.00 | 20.00 |
| N/A | N-Ethylpyrrolidone | 119.84 | 23.97 |
| N/A | BHT | 0.5 | 0.10 |
|  | TOTAL | 500.0 | 100.00 |

The N-methylpyrrolidone and N-Ethylpyrrolidone were added to a >500 ml beaker. Imidacloprid was added to the beaker while mixing. With continued mixing, permethrin (pre-heated to 54° C.) was added to the main mixture, followed by the addition of pyriproxyfen (pre-heated to 54° C.). BHT and urea were added separately to the beaker with constant mixing after each addition until a clear homogenous solution was formed (about 1 hour).

The composition was stored/frozen at a temperature of −23.3° C. for about 24 hours and then thawed. No crystal formation was observed after the initial freeze/thaw cycle.

The freeze/thaw cycle was repeated two additional times, and only minimal crystal formation was observed after the third freeze/thaw cycle.

Example 4—an Imidacloprid/Permethrin/Pyriproxyfen Spot-on Pesticide Composition Comprising 0.4% Urea A spot-on pesticide composition can be made in accordance with the formulation provided in Table 4:

TABLE 4

Spot-on Pesticide Composition Comprising Imidacloprid, Permethrin, Pyriproxifen, and 0.4% Urea

| Purity | Ingredient | Amount for 500 gm | Purity Adjusted Concentration (%) |
|---|---|---|---|
| 96.4 | Imidacloprid (98.3%) | 45.58 | 9.12 |
| 95.3 | Permethrin (95.2%) | 230.35 | 46.07 |
| 98.7 | Pyriproxyfen (98.7%) | 2.23 | 0.45 |
| N/A | Urea | 2.00 | 0.40 |

TABLE 4-continued

Spot-on Pesticide Composition Comprising Imidacloprid, Permethrin, Pyriproxifen, and 0.4% Urea

| Purity | Ingredient | Amount for 500 gm | Purity Adjusted Concentration (%) |
|---|---|---|---|
| N/A | N-methylpyrrolidone | 100.00 | 20.00 |
| N/A | N-Ethylpyrrolidone | 119.34 | 23.87 |
| N/A | BHT | 0.5 | 0.10 |
|  | TOTAL | 500.0 | 100.00 |

The N-methylpyrrolidone and N-Ethylpyrrolidone were added to a >500 ml beaker. Imidacloprid was added to the beaker while mixing. With continued mixing, permethrin (pre-heated to 54° C.) was added to the main mixture, followed by the addition of pyriproxyfen (pre-heated to 54° C.). BHT and urea were added separately to the beaker with constant mixing after each addition until a clear homogenous solution was formed (about 1 hour).

The composition was stored/frozen at a temperature of −23.3° C. for about 24 hours and then thawed. No crystal formation was observed after the initial freeze/thaw cycle.

The freeze/thaw cycle was repeated two additional times, and only minimal crystal formation was observed after the third freeze/thaw cycle.

Example 5—an Imidacloprid/Permethrin/Pyriproxyfen Spot-on Pesticide Composition Comprising 0.8% Urea A spot-on pesticide composition can be made in accordance with the formulation provided in Table 5:

TABLE 5

Spot-on Pesticide Composition Comprising Imidacloprid, Permethrin, Pyriproxifen, and 0.8% Urea

| Purity | Ingredient | Amount for 500 gm | Purity Adjusted Concentration (%) |
|---|---|---|---|
| 96.4 | Imidacloprid (98.3%) | 45.58 | 9.12 |
| 95.3 | Permethrin (95.2%) | 230.35 | 46.07 |
| 98.7 | Pyriproxyfen (98.7%) | 2.23 | 0.45 |
| N/A | Urea | 4.00 | 0.80 |
| N/A | N-methylpyrrolidone | 100.00 | 20.00 |
| N/A | N-Ethylpyrrolidone | 117.34 | 23.47 |
| N/A | BHT | 0.5 | 0.10 |
|  | TOTAL | 500.0 | 100.00 |

The N-methylpyrrolidone and N-ethylpyrrolidone were added to a >500 ml beaker. Imidacloprid was added to the beaker while mixing. With continued mixing, permethrin (pre-heated to 54° C.) was added to the main mixture, followed by the addition of pyriproxyfen (pre-heated to 54° C.). BHT and urea were added separately to the beaker with constant mixing after each addition until a clear homogenous solution was formed (about 1 hour).

The composition was then stored/frozen at −23.3° C. for about 24 hours, and then thawed. It was observed that the thawed solution was initially cloudy but cleared up. It was further observed that two small crystals remained in the solution after thawing. The freeze/thaw cycle was repeated two additional times. It was observed that additional crystals were observed in the solution following the second freeze/thaw cycle, and a considerable number of crystals remained in the solution following the third freeze/thaw cycle.

Example 6—an Imidacloprid/Permethrin/Pyriproxyfen Spot-on Pesticide Composition Comprising 0.5% Urea A spot-on pesticide composition comprising 0.5% urea was made in accordance with the formulation provided in Table 6:

TABLE 6

Spot-on Pesticide Composition Comprising Imidacloprid, Permethrin, Pyriproxifen, and 0.5% Urea

| Purity | Ingredient | Amount for 500 gm | Purity Adjusted Concentration (%) |
|---|---|---|---|
| 96.4 | Imidacloprid (98.3%) | 45.58 | 9.12 |
| 95.3 | Permethrin (95.2%) | 230.35 | 46.07 |
| 98.7 | Pyriproxyfen (98.7%) | 2.23 | 0.45 |
| N/A | Urea | 2.50 | 0.50 |
| N/A | N-methylpyrrolidone | 100.00 | 20.00 |
| N/A | N-Ethylpyrrolidone | 118.84 | 23.77 |
| N/A | BHT | 0.5 | 0.10 |
|  | TOTAL | 500.0 | 100.00 |

The N-methylpyrrolidone and N-ethylpyrrolidone were added to a >500 ml beaker. Imidacloprid was added to the beaker while mixing. With continued mixing, permethrin (pre-heated to 54° C.) was added to the main mixture, followed by the addition of pyriproxyfen (pre-heated to 54° C.). BHT and urea were added separately to the beaker with constant mixing after each addition until a clear homogenous solution was formed (about 1 hour).

The composition was then stored/frozen at −23.3° C. for about 24 hours, and then thawed. It was observed that the thawed solution contained some crystals. The freeze/thaw cycle was repeated two additional times. It was observed that additional crystals remained in the solution following the second freeze/thaw cycle, and a considerable number of crystals remained in the thawed solution following the third freeze/thaw cycle.

Example 7—Repeat Preparation of Imidacloprid/Permethrin/Pyriproxyfen Pesticide Composition Comprising 0.4% Urea and Freeze/Thaw Preparation of a spot-on pesticide composition comprising 0.4% urea was made in accordance with the formulation provided in Table 7:

TABLE 7

Spot-on Pesticide Composition Comprising Imidacloprid, Permethrin, and Pyriproxifen, and 0.4% Urea

| Purity | Ingredient | Amount for 1500 gm | Purity Adjusted Concentration (%) |
|---|---|---|---|
| 101.8 | Imidacloprid (98.3%) | 140.97 | 9.40 |
| 95.3 | Permethrin (95.2%) | 692.57 | 46.17 |
| 98.7 | Pyriproxyfen (98.7%) | 6.69 | 0.45 |
| N/A | Urea | 6.00 | 0.40 |
| N/A | N-methylpyrrolidone | 300.00 | 20.00 |
| N/A | N-Ethylpyrrolidone | 352.28 | 23.49 |
| N/A | BHT | 1.5 | 0.10 |
|  | TOTAL | 1500.00 | 100.00 |

The N-methylpyrrolidone was added to a >1000 ml beaker, followed by adding N-ethylpyrrolidone to the beaker with mixing. Imidacloprid was added to the beaker with continued mixing. With continued mixing, urea was added to the beaker, followed by BHT, permethrin (pre-heated to 54° C.), and pyriproxyfen (pre-heated to 54° C.). The solution was mixed until a clear homogenous solution was formed.

The composition was subjected to six freeze/thaw cycles as described in the Examples above. It was observed that the solution remained clear with no crystal formation being observed at any point in time during the six freeze/thaw cycles.

Example 8—Comparative Formulation: Imidacloprid/Permethrin/Pyriproxyfen Pesticide Composition Comprising Citric Acid Citric acid has been commonly used in spot-on formulations. A spot-on pesticide composition was prepared using a solvent system comprising citric acid (a highly dissociated acid), in lieu of urea (a highly dissociated base). The composition was prepared as described in Examples 1 through 6 above, using a concentration of 0.1% citric acid in the final composition. The composition was subjected to a freeze/thaw cycle as described in Examples 1 through 6 above. It was observed that extensive crystal formation occurred following each freeze/thaw cycle.

Example 9—Efficacy Evaluation of a Spot-on Composition of Example 4 Before and after Freeze/Thaw Cycles for the Treatment of Fleas and Ticks on Dogs The effect of multiple freeze/thaw cycles on the efficacy of a formulation of Example 4 for treating fleas and ticks on dogs will be evaluated. In short, a controlled study will be performed to evaluate the efficacy of the spot-on formulation after three freeze/thaw cycles, in comparison with the efficacy of the formulation before the freeze/thaw cycles.

Dogs will be randomized into one of three treatment groups. Group A, which will be the control group, will not receive any treatment for fleas and ticks and will be used as a point of comparison against the active treatment regimens. Group B comprised an active treatment group that will receive treatment with the spot-on formulation of Example 4 that had been subjected to the freeze/thaw cycles. Finally, Group C comprised an active treatment group that will receive treatment with the spot-on formulation of Example 4 that had not been subjected to the freeze/thaw cycles.

For all active treatments, a spot-on application will be developed and applied to the dogs in a manner in accordance with this invention. All dogs admitted into the experiment will first be deemed to be suffering from both flea and tick infestation. The experiment will be designed such that all treatment groups will be administered the appropriate treatment and then observed over time. During the post-application observation periods, dead ticks and fleas on and around the dogs will be counted for comparison between the various treatment groups, to determine the reduction in pests following treatment. In addition, the number of ticks and fleas remaining on the dog, within the observation areas, will also be determined.

The dogs of each group (Group A, Group B, and Group C) will be infested with fleas and ticks one day before treatment, and on various days after treatment for the two active treatment groups (Group B and Group C). The protocol will be designed to test the efficacy of the two treatments in regard to subsequent infestation after an initial treatment with an active spot-on composition. After the initial infestation, the dogs will again be infested with fleas in four intervals on the first day of each week (Day 7, 14, 21, and 28) for a period of approximately 4 weeks, with monitoring through Day 30. For each subsequent infestation, the dogs of each treatment group will be monitored to determine the kill rates for fleas (*Ctenophalides felis*) and ticks (*Rhipicephalus sanguineus*) at one hour after infestation, four hours after infestation, one day (24 hours) after infestation, and two days (48 hours) after infestation.

It is predicted that there will be no difference in average flea and tick kill rates between Group B and Group C dogs one hour and four hours after infestation for all infestation periods (Days 7, 14, 21, and 28). At all re-infestation intervals, Group B and Group C dogs will experience similar average reductions in the number of fleas and ticks present at one and four hours post re-infestation. Thus, the results of this example will illustrate that a formulation of Example 4 can be treated with multiple freeze/thaw cycles without affecting the efficacy of the formulation.

Example 10—Efficacy Evaluation of a Spot-on Composition of Example 4 Before and after Freeze/Thaw Cycles for the Treatment of Fleas and Ticks on Cats The effect of multiple freeze/thaw cycles on the efficacy of a formulation of Example 4 for treating fleas and ticks on cats will also be evaluated. In short, the experiments as described in Example 9 will be performed using cats instead of dogs. Similar results are predicted to be obtained using cat subjects. There will be no difference in average flea and tick kill rates between Group B and Group C cats one hour and four hours after infestation for all infestation periods (Days 7, 14, 21, and 28). At all re-infestation intervals, Group B and Group C cats will experience similar average reductions in the number of fleas and ticks present at one and four hours post re-infestation. Thus, the results of this example will illustrate that a formulation of Example 4 can be treated with multiple freeze/thaw cycles without affecting the efficacy of the formulation.

Example 11—Efficacy Evaluation of a Spot-on Composition of Example 4 and a Spot-on Composition of Example 8 after Freeze/Thaw Cycles for the Treatment of Fleas and Ticks on Dogs and Cats The effect of one or more freeze/thaw cycles on the efficacy of a formulation of Example 4 and a formulation of Example 8 for treating fleas and ticks on animals (cats and dogs) will be evaluated. Dogs and cats will be randomized into one of three treatment groups. Group A, which will be the control group, will not receive any treatment for fleas and ticks and will be used as a point of comparison against the active treatment regimens. Group B will comprised an active treatment group that will receive treatment with the spot-on formulation of Example 4 that had been subjected to multiple freeze/thaw cycles. Finally, Group C will comprise an active treatment group that will received treatment with the spot-on formulation of Example 8 that had been subjected to a single freeze/thaw cycles.

For all active treatments, a spot-on application will be developed and applied to the dogs in a manner in accordance with this invention. All animals admitted into the experiment will first be deemed to be suffering from both flea and tick infestation. The experiment will be designed such that all treatment groups will be administered the appropriate treatment and then observed over time. During the post-application observation periods, dead ticks and fleas on and around the animals will be counted for comparison between the various treatment groups, to determine the reduction in pests following treatment. In addition, the number of ticks and fleas remaining on the animals, within the observation areas, will also be determined.

Group B animals, which received the spot-on formulation of Example 4 that had been subjected to multiple freeze/thaw cycles is predicted to experience similar kill rates as shown in Example 10 one hour and four hours after infestation for all infestation periods (Days 7, 14, 21, and 28). At all re-infestation intervals, Group B animals are predicted to experienced similar average reductions in the number of fleas and ticks present at one and four hours post re-infestation. Conversely, Group C animals which will receive the spot-on formulation of Example 8 that had been subjected to a single freeze/thaw cycle are predicted to experience significantly reduced kill rates when compared to Group B animals for all periods. Thus, the results of this example will illustrate that a formulation of Example 4 can be treated with multiple freeze/thaw cycles without affecting the efficacy of the formulation, whereas a formulation of Example 8 which uses a commonly-used solvent comprising citric acid had significantly reduced efficacy after even a single freeze/thaw cycle.

The disclosures of each patent, patent application and publication cited or described in this document are hereby incorporated herein by reference, in their entirety.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A spot-on pesticide composition for controlling pests on animals, the composition consisting of two or more active pesticidal compounds and a solvent system, wherein the solvent system consists of urea, N-methylpyrrolidone (NMP), and N-ethylpyrrolidone (NEP) and wherein the composition optionally comprises an insect growth regulator and an antioxidant.

2. The spot-on pesticide composition of claim 1, wherein the composition consists of between about 50% to about 60% (w/w) of the two or more active pesticidal compounds and between about 40% to about 50% (w/w) of the solvent system.

3. The spot-on pesticide composition of claim 2, wherein the solvent system consists of between about 0.5% and about 1.5% (w/w) urea, between about 40% and about 70% (w/w) NMP, and between about 30% and about 60% (w/w) NEP.

4. The solvent system of claim 3, wherein the solvent system consists of between about 0.7% to about 1.2% (w/w) urea.

5. The solvent system of claim 3, wherein the solvent system consists of between about 52% and about 57% (w/w) NEP, between about 52% and about 57% (w/w) NMP, and between about 0.3% and about 0.5% (w/w) urea.

6. The spot-on pesticide composition of claim 1, wherein the two or more active pesticidal compounds comprises a neonicotinoid and a pyrethroid.

7. The spot-on pesticide composition of claim 6, wherein the two or more active pesticidal compounds comprises between about 10% to about 30% (w/w) of a neonicotinoid and between about 70% to about 90% (w/w) of a pyrethroid.

8. The spot-on pesticide composition of claim 1, wherein the two or more active pesticidal compounds comprises between about 10% to about 30% (w/w) of a neonicotinoid, between about 70% to about 90% (w/w) of a pyrethroid, and about 0% to about 5% (w/w) of an insect growth regulator.

9. The spot-on pesticide composition of claim 1, wherein the two or more active pesticidal compounds comprises between about 1% to about 20% (w/w) of a neonicotinoid and between about 1% to about 70% (w/w) of a pyrethroid.

10. The spot-on pesticide composition of claim 9, wherein the neonicotinoid is selected from the group consisting of imidacloprid, acetamiprid, nithiazine, thiamethoxam, dinotefuran, nitenpyram, thiacloprid, clothianadin, and combinations thereof.

11. The spot-on pesticide composition of claim 9, wherein the neonicotinoid is imidacloprid.

12. The spot-on pesticide composition of claim 11, wherein the two or more active pesticidal compounds comprises between about 5% to about 15% (w/w) imidacloprid.

13. The spot-on pesticide composition of claim 9, wherein the pyrethroid is selected from the group consisting of permethrin, cypermethrin, cyphenothrin, etofenprox, fenvalerate, cyfluthrin, and combinations thereof.

14. The spot-on pesticide composition of claim 13, wherein the pyrethroid is permethrin.

15. The spot-on pesticide composition of claim 14, wherein the two or more active pesticidal compounds comprises between about 40% to about 50% (w/w) permethrin.

16. The spot-on pesticide composition of claim 9, wherein the two or more active pesticidal compounds further comprises between about 0.01% and about 20% (w/w) of an insect growth regulator.

17. The spot-on pesticide composition of claim 1, wherein the composition further consists of between about 0% and about 10% (w/w) of an antioxidant selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, p-aminobenzoic acid (PABA), butylated hydroxyanisole (BHA), butylated hydroxytoluene (BHT), and combinations thereof.

18. The spot-on pesticide composition of claim 17, wherein the antioxidant is BHT.

19. The spot-on pesticide composition of claim 16, wherein the insect growth regulator is a juvenile hormone mimic, a chitin synthesis inhibitor, and combinations thereof.

20. The spot-on pesticide composition of claim 19, wherein the insect growth regulator is selected from the group consisting of S-methoprene, pyriproxyfen, novaluron, and combinations thereof.

21. The spot-on pesticide composition of claim 20, wherein the insect growth regulator is pyriproxyfen.

22. The spot-on pesticide composition of claim 1, wherein the solvent system consists of between about 40% to about 70% (w/w) NEP, between about 30% to about 60% (w/w) NMP, and between about 0.1% and about 5% (w/w) urea.

23. The spot-on pesticide composition of claim 1, wherein the composition consists of between about 7.5% and about 9.5% (w/w) imidacloprid, between about 42% and about 46% (w/w) permethrin, between about 0.4% to about 0.5% (w/w) pyriproxyfen, between about 0.05% and about 1.5% (w/w) BHT, and about 44% (w/w) of a solvent system consisting of between about 22% to about 26% (w/w of the overall composition) NEP, between about 18% to about 22% (w/w of the overall composition) NMP, and between about 0.3% and about 0.5% (w/w of the overall composition) urea.

24. A spot-on pesticide composition consisting of between about 1% and about 20% (w/w) of a neonicotinoid, between about 1% and about 70% (w/w) of a pyrethroid, between about 0.01% and about 20% (w/w) of an insect growth regulator, between about 0.01% and about 10% (w/w) of an antioxidant, and between about 10% and about 98% (w/w) of a solvent system consisting of urea, NMP, and NEP.

25. A solvent system for improved storage stability of spot-on pesticide compositions, wherein the solvent system consists of between about 0.5% and about 1.5% (w/w) urea, between about 40% and about 70% (w/w) NEP, and between about 30% and about 60% (w/w) NMP.

26. A method of killing insect and pest pupae and adults on an animal, which method comprises administering a localized cutaneous application between the shoulders of the animal, a spot-on composition consisting of between about 1% and about 20% (w/w) of a neonicotinoid, between about 1% and about 70% (w/w) of a pyrethroid, optionally between about 0.01% and about 20% (w/w) of an insect growth regulator, optionally between about 0.01% and about 10% (w/w) of an antioxidant, and between about 10% and about 98% (w/w) of a solvent system consisting of urea, NMP, and NEP.

27. The method of claim 26, wherein the spot-on composition consists of between about 7.5% and about 9.5% (w/w) imidacloprid, between about 42% and about 46% (w/w) permethrin, between about 0.4% to about 0.5% (w/w) pyriproxyfen, between about 0.05% and about 1.5% (w/w) BHT, and about 44% (w/w) of a solvent system, the solvent system consisting of between about 22% to about 26% (w/w of the overall composition) NEP, between about 18% to about 22% (w/w of the overall composition) NMP, and between about 0.3% and about 0.5% (w/w of the overall composition) urea.

28. The method of claim 26, wherein the animal is a mammal.

29. The method of claim 28, wherein the mammal comprises a dog or a cat.

* * * * *